US 7,456,308 B2

(12) United States Patent
Nguyen et al.

(10) Patent No.: US 7,456,308 B2
(45) Date of Patent: *Nov. 25, 2008

(54) GRIGNARD PROCESSES WITH IMPROVED YIELDS OF DIPHENYLCHLOROSILANES AS PRODUCTS

(75) Inventors: Binh Thanh Nguyen, Midland, MI (US); Curtis John Bedbury, Midland, MI (US); Roger Edwin Humburg, Midland, MI (US); Susan Mary Jacob, Midland, MI (US); Sarah Jane Ratcliff, Midland, MI (US); John Dennis Waterman, Coleman, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/585,154

(22) PCT Filed: Dec. 17, 2004

(86) PCT No.: PCT/US2004/043005

§ 371 (c)(1), (2), (4) Date: Jun. 29, 2006

(87) PCT Pub. No.: WO2005/068475

PCT Pub. Date: Jul. 28, 2005

(65) Prior Publication Data

US 2007/0066826 A1    Mar. 22, 2007

Related U.S. Application Data

(60) Provisional application No. 60/534,443, filed on Jan. 6, 2004.

(51) Int. Cl.
C07F 7/04 (2006.01)
(52) U.S. Cl. .................................... 556/480; 546/14
(58) Field of Classification Search ................. 556/480; 546/14
See application file for complete search history.

(56) References Cited

U.S. PATENT DOCUMENTS

| 2,426,122 A | 8/1947 | Rust et al. |
| 2,795,627 A | 6/1957 | Ramsden et al. |
| 2,795,628 A | 6/1957 | Ramsden et al. |
| 2,816,937 A | 12/1957 | Ramsden et al. |
| 2,894,012 A | 7/1959 | Ramsden et al. |
| 3,095,460 A | 6/1963 | Olah et al. |
| 3,140,321 A | 7/1964 | Goepfert et al. |
| 3,264,360 A | 8/1966 | Nudenberg et al. |
| 3,485,863 A | 12/1969 | Nutzel et al. |
| 4,127,507 A | 11/1978 | Fannin et al. |
| 4,593,112 A | 6/1986 | Takamizawa et al. |
| 4,687,874 A | 8/1987 | Oswald et al. |
| 4,921,989 A | 5/1990 | Ishihara et al. |
| 5,099,040 A | 3/1992 | Rosen et al. |
| 5,242,625 A | 9/1993 | Jones et al. |
| 5,596,120 A | 1/1997 | Bank et al. |
| 5,606,088 A | 2/1997 | Bank et al. |
| 5,629,439 A | 5/1997 | Bank et al. |
| 6,057,480 A | 5/2000 | Ueno et al. |
| 6,541,651 B1 * | 4/2003 | Bedbury et al. .............. 556/480 |
| 6,552,237 B1 * | 4/2003 | Bedbury et al. .......... 568/909.5 |
| 6,686,492 B2 * | 2/2004 | Nguyen ...................... 556/480 |
| 7,084,206 B2 * | 8/2006 | Bedbury et al. ............. 524/858 |
| 2003/0191238 A1 | 10/2003 | Bedbury et al. |
| 2005/0068475 A1 | 3/2005 | Kume et al. |
| 2005/0068476 A1 | 3/2005 | Okabe |

FOREIGN PATENT DOCUMENTS

| DE | 243028 | 2/1987 |
| DE | 243031 | 2/1987 |
| EP | 0825195 | 2/1998 |
| EP | 0729931 | 8/1998 |
| GB | 622970 | 1/1947 |
| GB | 622970 * | 5/1949 |
| GB | 657704 | 9/1951 |
| GB | 1120150 | 7/1968 |
| JP | 62-022790 | 1/1987 |

(Continued)

OTHER PUBLICATIONS

Emeleus et al., Journal of the Chemical Society (1947), 1592-1594.*

(Continued)

*Primary Examiner*—Daniel M Sullivan
*Assistant Examiner*—Chukwuma O Nwaonicha
(74) *Attorney, Agent, or Firm*—Patricia M. Scaduto

(57) ABSTRACT

A Grignard process for preparing phenyl-containing chlorosilane products, in particular diphenylchlorosilanes, is carried out in three embodiments. In the first embodiment, the reactants of the Grignard process are a phenyl Grignard reagent, an ether solvent, a trichlorosilane, and an aromatic hydrocarbon coupling solvent. In the second embodiment, the reactants of the Grignard process are a phenyl Grignard reagent, an ether solvent, a phenylchlorosilane, and an aromatic hydrocarbon coupling solvent. In the third embodiment, the reactants of the Grignard process are a phenyl Grignard reagent, an ether solvent, a trichlorosilane, a phenylchlorosilane, and an aromatic hydrocarbon coupling solvent. In each embodiment, the reactants are present in a particular mole ratio.

4 Claims, No Drawings

FOREIGN PATENT DOCUMENTS

| | | |
|---|---|---|
| JP | 03-109389 | 5/1991 |
| JP | 08-245641 | 9/1996 |
| JP | 08333374 | 12/1996 |
| RU | 2174124 | 9/2001 |
| SU | 477626 | 8/1985 |
| WO | WO 03/084901 | 10/2003 |
| WO | WO 03/084967 | 10/2003 |
| WO | WO 03/084970 | 10/2003 |
| WO | WO 03/106465 | 12/2003 |
| WO | WO 2005/068475 | 7/2005 |
| WO | WO 2005/068476 | 7/2005 |
| WO | WO 2006/083665 | 8/2006 |

OTHER PUBLICATIONS

Lennon, Patrick J. et al: "Nuclephilic catalysis of organosilicon substitution reactions" Organometallics, 8(4), 1121-2 CODEN: ORGND7; ISSN: 0276-7333, 1989, XP002322018.

Semenov V. V. et al., Reactions of Methylchlorodisilanes with Grignard Reagents, Russian Chemical Bulletin, vol 44, No. 5, 1995, pp. 927-930.

Kunai, A. et al.: "Highly selective synthesis of chlorosilanes from hydrosilanes", Organometallics, 11(7), pp. 2708-2711, 1992, XP009068024.

Hyde, J. F. et al: "Condensation products of the organo-silane diols", Journal of the American Chemical Society, 63(5), May 1941, pp. 1194-1196, XP009068013.

Tuulmets, et al., Partially Solanted Alkylmagnesium Chlorides in Toluene, Jur. Of Organometallic Chem., vol. 523, Oct. 18, 1996, pp. 133-138.

Tuulmets, et al., Solvation Effects in Partially Solvated Grignard Reagents, Jour. Of Organometallic Chem., vol. 575 (1999) pp. 182-186.

Coates et al., Organomethallic Compounds, vol. 1, pp. 76-103, 1967, Methuen and Co. Ltd, London, U.K.

Kirk/Orthmer, Encyclopedia of Chemical Technology, vol. 10, 721-734 (1966) The interscience Encylopedia, Inc., NY NY.

Turk, et al., Organic Systhesis, vol. 27, 7-8 (1947).

Tuulmets A. et al., Gringnard Reagents in Toulene Solutions, Applied Organometallic Chemistry, vol. 16, Jul. 23, 2002, pp. 525-529.

Tuulmets A. et al., Reactions of partially solvated Grignard reagents with a ketone, Journal of Organometallic Chemistry Elsevier-Sequoia S.A. Lausanne, CH, vol. 586, No. 2, Sep. 5, 1999 pp. 145-149.

Tuulmets A. et al., Influence of sonication of Grignard reagent formation, Ultrasonics: Sonochemistry, Butterworth-Heinemann, GB, vol. 2, No. 2, Oct. 1, 1995, pp. S75-S78.

Kolodyazhnyi Y. V. et al., Structure and Donor Activity in Organometallic Compounds, Jouranl of General Chemistry of the USSR, vol. 52, No. 3, 1982, pp. 554-558.

* cited by examiner

GRIGNARD PROCESSES WITH IMPROVED YIELDS OF DIPHENYLCHLOROSILANES AS PRODUCTS

CROSS REFERENCE TO RELATED APPLICATIONS

This application is a U.S. national stage filing under 35 U.S.C. §371 of PCT Application Ser. No. PCT/US04/043005 filed on 17 Dec. 2004, currently pending, which claims the benefit of U.S. Provisional Patent Application No. 60/534,443 filed 06 Jan. 2004 under 35 U.S.C. §119 (e). PCT Application No. PCT/US04/043005 and U.S. Provisional Patent Application No. 60/534443 are hereby incorporated by reference.

DESCRIPTION

This invention is related to Grignard processes for preparing phenyl-containing chlorosilane products. In particular, it relates to Grignard processes in which the yield of diphenylchlorosilanes as a product is maximized and the yield of phenylchlorosilanes as a product is minimized.

In U.S. Pat. No. 6,541,651 (Apr. 1, 2003) entitled "Process for Chlorosilane Intermediate Manufacture", (the '651 patent hereafter), assigned to the same assignee as the present invention, a Grignard process is described in which the yield of phenylchlorosilanes as a product is maximized and the yield of diphenylchlorosilanes as a product is minimized. In fact, the diphenylchlorosilanes prepared in the '651 patent are only present as by-products.

This invention in contrast, is characterized in that it seeks to obtain an opposite result, i.e., to minimize the yield of phenylchlorosilanes as a product while maximizing the yield of diphenylchlorosilanes as a product. Achievement of this goal is obtained by carrying out the Grignard process using certain mole ratios of the reactants used in the Grignard process.

This invention relates to Grignard processes for preparing diphenylchlorosilanes in a maximum yield and phenylchlorosilanes in a minimum yield. In a first embodiment, the reactants of the Grignard process comprise a phenyl Grignard reagent, an ether solvent, a trichlorosilane, and an aromatic hydrocarbon coupling solvent. In this first embodiment, the phenyl Grignard reagent is preferably phenyl magnesium chloride; the ether solvent is a dialkyl ether such as dimethyl ether, diethyl ether, ethylmethyl ether, n-butylmethyl ether, n-butylethyl ether, di-n-butyl ether, di-isobutyl ether, isobutylmethyl ether, and isobutylethyl ether; the aromatic solvent is preferably toluene; and the trichlorosilane is preferably methyltrichlorosilane, phenyltrichlorosilane, or vinyltrichlorosilane.

In a second embodiment, the reactants of the Grignard process comprise a phenyl Grignard reagent, an ether solvent, a phenylchlorosilane, and an aromatic hydrocarbon coupling solvent. In this second embodiment, the phenyl Grignard reagent, ether solvent, and aromatic hydrocarbon coupling solvent are the same as noted above; and the phenylchlorosilane is preferably phenylmethyldichlorosilane, phenyltrichlorosilane, diphenyldichlorosilane, phenylvinyldichlorosilane, or hydridophenyldichlorosilane.

In a third embodiment, the reactants of the Grignard process comprise a phenyl Grignard reagent, an ether solvent, a trichlorosilane, a phenylchlorosilane, and an aromatic hydrocarbon coupling solvent. In this third embodiment, the preferred reactants are the same as noted above in the second and third embodiments.

In the first embodiment, the mole ratio of the ether solvent to the phenyl Grignard reagent is 2 to 5, the mole ratio of the trichlorosilane to the phenyl Grignard reagent is 0.1 to 10, and the mole ratio of the aromatic coupling solvent to the phenyl Grignard reagent is 3 to 7. In the second embodiment, the mole ratio of the ether solvent to the phenyl Grignard reagent is 2 to 5, the mole ratio of the phenylchlorosilane to the phenyl Grignard reagent is 0.5 to 5, and the mole ratio of the aromatic coupling solvent to the phenyl Grignard reagent is 3 to 7. In the third embodiment, the mole ratio of the ether solvent to the phenyl Grignard reagent is 2 to 5, the mole ratio of the trichlorosilane to the phenyl Grignard reagent is 0.1 to 10, the mole ratio of the phenylchlorosilane to the phenyl Grignard reagent is 0.5 to 5, and the mole ratio of the aromatic coupling solvent to the phenyl Grignard reagent is 3 to 7.

These and other features of the invention will become apparent from a consideration of the detailed description.

As used herein, the term normal coupling refers to reactions of a phenyl Grignard reagent chloride with a trichlorosilane; the term co-coupling refers to reactions of the phenyl Grignard reagent the trichlorosilane and a phenylchlorosilane; and the term direct coupling refers to reactions of the phenyl Grignard reagent with the phenylchlorosilane.

The Grignard process employed according to this invention, and as generally depicted in the '651 patent, is illustrated below in chemical reactions (I) and (II). This represents the first embodiment of the invention, i.e., normal coupling. Toluene is one of the products of chemical reaction (II) but is not shown in the reaction.

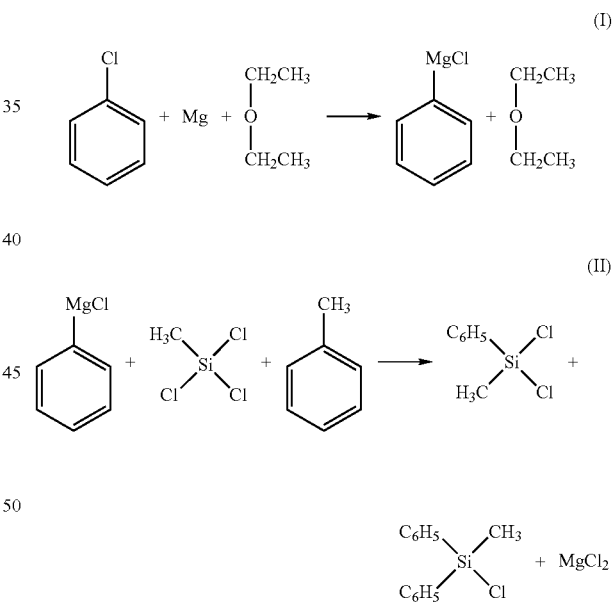

In chemical reaction (I), phenyl chloride/chlorobenzene (PhCl) is combined with magnesium metal (Mg) in the presence of the solvent diethyl ether ($CH_3CH_2$—O—$CH_2CH_3$), to form phenyl magnesium chloride (PhMgCl) in diethyl ether. Phenyl magnesium chloride in diethyl ether is then used in chemical reaction (II) where it is combined with methyltrichlorosilane ($MeSiCl_3$) and the coupling solvent toluene. The products of chemical reaction (II) are phenylmethyldichlorosilane ($PhMeSiCl_2$), diphenylmethylchlorosilane ($Ph_2MeSiCl$), magnesium chloride, and toluene.

The second embodiment of the invention, i.e., direct coupling, is essentially the same as the first embodiment (normal coupling) depicted above in chemical reactions (I) and (II), except that in the second embodiment, phenylmethyldichlorosilane is used instead of methyltrichlorosilane, as shown below in chemical reaction (III). Toluene is one of the products of chemical reaction (III) but is not shown in the reaction.

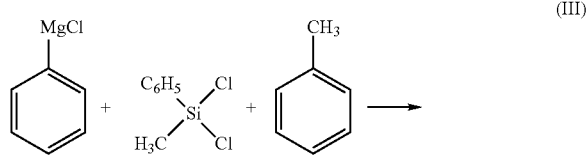

(III)

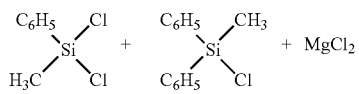

According to the third embodiment of the invention, i.e., co-coupling, depicted below as chemical reaction (IV), chemical reactions (II) and (III) are essentially replicated, with the proviso that in chemical reaction (II), phenylmethyldichlorosilane is added as a reactant with methyltrichlorsilane, and in chemical reaction (III), methyltrichlorosilane is added as a reactant with phenylmethyldichlorosilane. Toluene is one of the products of chemical reaction (IV) but is not shown in the reaction.

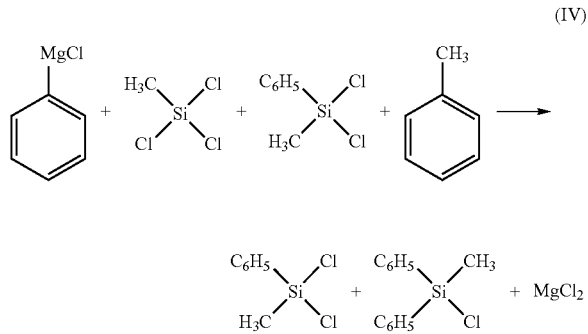

(IV)

The differences between the process described in this invention in comparison to the process described in the common assignee's '651 patent, are shown below in Tables I and II. In the Tables, it can be seen that according to the first embodiment of this invention, the mole ratio of PhMgCl/ether/MeSiCl$_3$/toluene is 1/4/0.5/5, respectively, compared to the corresponding mole ratio of PhMgCl/ether/MeSiCl$_3$/toluene in the '651 patent of 1/4/3/3.

The mole ratio in the second embodiment of the process according to this invention of PhMgCl/ether/PhMeSiCl$_2$/toluene is 1/4/1.1/1.3, respectively, whereas the corresponding mole ratio of PhMgCl/ether/PhMeSiCl$_2$/toluene in the '651 patent is indeterminate and undisclosed.

The mole ratio in the third embodiment of the process according to this invention of PhMgCl/ether/MeSiCl$_3$/PhMeSiCl$_2$/toluene is 1/4/1.2/0.3/3, respectively, whereas the corresponding mole ratio of PhMgCl/ether/MeSiCl$_3$/PhMeSiCl$_2$/toluene in the '651 patent is indeterminate and undisclosed.

TABLE I

| | Present Invention | | | | |
|---|---|---|---|---|---|
| Embodiment | Mole Ratio PhMgCl | Mole Ratio Ether | Mole Ratio MeSiCl$_3$ | Mole Ratio PhMeSiCl$_2$ | Mole Ratio Toluene |
| I | 1 | 4 | 0.5 | — | 5 |
| II | 1 | 4 | — | 1.1 | 3 |
| III | 1 | 4 | 1.2 | 0.3 | 3 |

TABLE II

| | U.S. Pat. No. 6,541,651 | | | | |
|---|---|---|---|---|---|
| Embodiment | Mole Ratio PhMgCl | Mole Ratio Ether | Mole Ratio MeSiCl$_3$ | Mole Ratio PhMeSiCl$_2$ | Mole Ratio Toluene |
| I | 1 | 4 | 3 | — | 3 |
| II | Indeterminate | Indeterminate | — | Indeterminate | Indeterminate |
| III | Indeterminate | Indeterminate | Indeterminate | Indeterminate | Indeterminate |

As noted above, these differences are significant, as the thrust and focus of the '651 patent is the production of phenylmethyldichlorosilane as the primary and major product of the reaction, whereas the thrust and focus of the present invention is the production of diphenylmethylchlorosilane as the primary and major product of the process. Thus, by following the teaching of the method according to this invention, it is possible for one skilled in the art to prepare products of the process containing about 14-18 percent by weight of diphenylmethylchlorosilane and only about 1-5 percent by weight of phenylmethyldichlorosilane, whereas the reverse of those amounts is generally the case according to the process in the '651 patent; although the '651 patent does not specifically set forth the exact amounts of each of the chlorosilanes present in the product.

Chlorosilanes useful according to the invention have the general formula $R_aSiX_{4-a}$ wherein each R can represent a phenyl group, methyl group, vinyl group, or hydrogen; X represents chlorine or bromine; and $a$ has a value of 0, 1, or 2. Some suitable and representative chlorosilanes which can be used include silicon tetrachloride, methyltrichlorosilane, dimethyldichlorosilane, phenylmethyldichlorosilane, phenyltrichlorosilane, diphenyldichlorosilane, vinyltrichlorosilane, hydridotrichlorosilane, divinyldichlorosilane, methylvinyldichlorosilane, phenylvinyldichlorosilane, hydridomethyldichlorosilane, hydridophenyldichlorosilane, hydridovinyldichlorosilane and dihydridodichlorosilane.

Magnesium metal useful in this invention can be any of the forms of the metal currently being used in Grignard-type reactions. For example, the metal can be in the form of a powder, flake, granule, chip, lump, or shaving. Contact of the magnesium metal with the phenyl halide can be undertaken in standard type reactors suitable for running Grignard type reactions. Thus, the reactor can be a batch, semi-batch, or continuous type reactor. A preferred reactor is a continuous reactor. The environment in which the present method is carried out should be inert for best results. Therefore, under preferred conditions of the method, the reactor is purged and blanketed with an inert gas such as nitrogen or argon.

Phenyl halides useful in this invention are those of the formula RX wherein R represents phenyl and X is a chlorine or bromine atom. The preferred phenyl halide for this invention is phenyl chloride (chlorobenzene). Solvents for synthesizing the Grignard reagent include dialkyl ethers such as dimethyl ether, diethyl ether, ethylmethyl ether, n-butylmethyl ether, n-butylethyl ether, di-n-butyl ether, di-isobutyl ether, isobutylmethyl ether, and isobutylethyl ether. The most preferred ether solvent is diethyl ether. However, aromatic solvents such as toluene are used as the coupling solvent in the coupling reaction of the phenyl Grignard reagent PhMgCl with PhMeSiCl$_2$ or MeSiCl$_3$ in processes of the invention. Phenyl Grignard reagents such as PhMgCl can either be synthesized or purchased commercially, as desired.

EXAMPLES

The following examples are set forth in order to illustrate the invention in more detail.

Example 1

Normal Coupling of PhMgCl with MeSiCl$_3$—Coupling Mole Ratio of 1/4/0.5/5 of PhMgCl/ether/MeSiCl$_3$/toluene—First Embodiment of the Invention A normal coupling reaction of PhMgCl/ether/MeSiCl$_3$/toluene was carried out at a mole ratio of 1/4/0.5/5 as follows. Methyltrichlorosilane and a Grignard solution containing PhMgCl and diethyl ether were synthesized in-house. The mole ratio of the Grignard solution was 1/4 PhMgCl/diethyl ether with a PhMgCl concentration of about 2 mol/L. The stock solution was in two phases consisting of a liquid containing solids that settled at the bottom. In this example, both the liquid and solid portions were used. Approximately 250 milliliter of the solution was transferred to a 500 milliliter addition funnel via a pump. This is the equivalent of about 0.500 mol PhMgCl and 2.00 mol of diethyl ether. Then, 37.37 gram (0.25 mol) of MeSiCl$_3$ and 230.38 gram (2.5 mol) of toluene were added to a 1000 milliliter round bottom flask.

The addition funnel was attached and a nitrogen source was connected to provide an inert atmosphere in the system. Addition of the Grignard solution took place over a time period of 13.5 minutes. The solution turned a dark orange brown color but remained flowable throughout the procedure. The maximum exothermic temperature reached during the procedure was 58° C. When agitation was stopped, the settling of solids began almost immediately. The percent mass recovery was 97.45 percent. Gas chromatography (GC) analysis of the reaction mixture showed a content of the product of 17.13 weight percent of desired component Ph$_2$MeSiCl and only 5.7 weight percent of PhMeSiCl$_2$. The weight ratio of Ph$_2$MeSiCl/PhMeSiCl$_2$ was 3.

Example 2

Direct Coupling of PhMgCl with PhMeSiCl$_2$—Coupling Mole Ratio of 1/4/1.1/3 of PhMgCl/ether/PhMeSiCl$_2$/toluene—Second Embodiment of the Invention A direct coupling reaction of PhMgCl/ether/PhMeSiCl$_2$/toluene was carried out at a mole ratio of 1/4/1.1/3 as follows. A Grignard solution containing PhMgCl and diethyl ether were synthesized in-house. The mole ratio of the Grignard solution was 1/4 PhMgCl/diethyl ether with a PhMgCl concentration of about 2 mol/L. The stock solution was in two phases consisting of a liquid containing solids that settled at the bottom. In this example, both the liquid and solid portions were used. Approximately 250 milliliter of the solution was transferred to a 500 milliliter addition funnel via a pump. This is the equivalent of about 0.500 mol PhMgCl and 2.00 mol of diethyl ether. Then, 105.55 gram (0.25 mol) of PhMeSiCl$_2$ and 138.71 gram (1.5 mol) of toluene were added to a 1000 milliliter round bottom flask.

The addition funnel was attached and a nitrogen source was connected to provide an inert atmosphere in the system. Addition of the Grignard solution took place over a time period of 10 minutes. The solution turned a dark orange brown color but remained flowable throughout the procedure. The maximum exothermic temperature reached during the procedure was 58° C. When agitation was stopped, the settling of solids began almost immediately. The percent mass recovery was 98.28 percent. Gas chromatography (GC) analysis of the reaction mixture showed a content of the product of 16.26 weight percent of desired component Ph$_2$MeSiCl and only 7.87 weight percent of PhMeSiCl$_2$. The weight ratio of Ph$_2$MeSiCl/PhMeSiCl$_2$ was 2.1.

Example 3

Co-Coupling with Mixture of MeSiCl$_3$ and PhMeSiCl$_2$—Coupling Mole Ratio of 1/4/1.2/0.3/3 of PhMgCl/ether/MeSiCl$_3$/PhMeSiCl$_2$/toluene—Third Embodiment of Invention A co-coupling reaction of PhMgCl/ether/MeSiCl$_3$/PhMeSiCl$_2$/toluene was carried out at a mole ratio of 1/4/1.2/0.3/3 as follows. A Grignard solution containing PhMgCl and diethyl ether were synthesized in-house. The mole ratio of the Grignard solution was 1/4 PhMgCl/diethyl ether with a PhMgCl concentration of about 2 mol/L. The stock solution was in two phases consisting of a liquid containing solids that settled at the bottom. In this example, both the liquid and solid portions were used. Approximately 250 milliliter of the solution was transferred to a 500 milliliter addition funnel via a pump. This is the equivalent of about 0.500 mol PhMgCl and 2.00 mol of diethyl ether. Then, 28.67 gram (0.15 mol) of PhMeSiCl$_2$, 89.68 gram (0.601 mol) of MeSiCl$_3$, and 138.05 gram (1.499 mol) of toluene were added to a 1000 milliliter round bottom flask.

The addition funnel was attached and a nitrogen source was connected to provide an inert atmosphere in the system. Addition of the Grignard solution took place over a time period of 10.5 minutes. The solution turned a dark orange brown color but remained flowable throughout the procedure. The maximum exothermic temperature reached during the procedure was 59° C. When agitation was stopped, the settling of solids began almost immediately. The reaction mixture was allowed to cool and transferred to a labeled sample jar. The percent mass recovery was 97.26 percent. Gas chromatography (GC) analysis of the reaction mixture showed a content of the product of 16.46 weight percent of desired component Ph$_2$MeSiCl and only 1.88 weight percent of PhMeSiCl$_2$. The weight ratio of Ph$_2$MeSiCl/PhMeSiCl$_2$ was 8.7.

It is generally known in the art that an increase in the formation of Ph$_2$MeSiCl by a coupling reaction of PhMgCl with PhMeSiCl$_2$ (direct coupling), or by the reaction of PhMgCl with MeSiCl$_3$ (normal coupling), is both difficult and not easily attainable. As shown above, however, it has been unexpectedly discovered according to this invention, that by changing the ratio of PhMgCl/MeSiCl$_3$ (normal coupling), or PhMgCl/PhMeSiCl$_2$ (direct coupling), or PhMgCl/MeSiCl$_3$ and PhMgCl/PhMeSiCl$_2$ (co-coupling), it is possible to not only improve, but to actually increase the production of $Ph_2MeSiCl$. This is significant, since it now enables those skilled in the art to increase and maximize the production of $Ph_2MeSiCl$, while at the same time minimizing the production of $PhMeSiCl_2$, by a processes not known heretofore.

Other variations may be made in compounds, compositions, and methods described herein without departing from the essential features of the invention. The embodiments of the invention specifically illustrated herein are exemplary only and not intended as limitations on their scope except as defined in the appended claims.

The invention claimed is:

1. A process for preparing diphenylchlorosilanes by the Grignard process comprising contacting a phenyl Grignard reagent, an ether solvent, a trichlorosilane selected from the group consisting of methyltrichlorosilane, phenyltrichlorosilane, and vinyltrichlorosilane, a phenylchlorosilane selected from the group consisting of phenylmethyldichlorosilane, phenyltrichlorosilane, diphenyldichlorosilane, phenylvinyldichlorosilane, and toluene; wherein the mole ratio of the ether solvent to the phenyl Grignard reagent is 2 to 5, the mole ratio of the trichlorosilane to the phenyl Grignard reagent is 0.1 to 10, the mole ratio of the phenylchlorosilane to the phenyl Grignard reagent is 0.5 to 5, and the mole ratio of toluene to the phenyl Grignard reagent is 3 to 7.

2. The process according to claim 1 wherein the phenyl Grignard reagent is phenyl magnesium chloride.

3. The process according to claim 1 wherein the ether solvent is a dialkyl ether selected from the group consisting of dimethyl ether, diethyl ether, ethylmenthyl ether, n-butylmethyl ether, n-butylethyl ether, di-n-butyl ether, di-isobutyl ether, isobutylmethyl ether, and isobutylethyl ether.

4. The process according to claim 1 wherein the mole ratio of the phenyl grignard reagent to the ether solvent to the trichlorosilane to the phenylchorosilane to the toluene is 1/4/1.2/0.3/3.

* * * * *